United States Patent [19]

Churchouse et al.

[11] Patent Number: 4,963,490

[45] Date of Patent: Oct. 16, 1990

[54] POROUS INORGANIC MEMBRANE SUPPORT AND METHOD

[75] Inventors: Stephen J. Churchouse; Elizabeth M. Scamans, both of Banbury, England

[73] Assignee: Alcan International Limited, Montreal, Canada

[21] Appl. No.: 239,502

[22] Filed: Sep. 1, 1988

[30] Foreign Application Priority Data

Sep. 7, 1987 [GB] United Kingdom ............... 8721018

[51] Int. Cl.$^5$ .................. C12N 5/00; C12M 3/00
[52] U.S. Cl. .................. 435/240.241; 435/240.23; 435/240.243; 435/284; 435/285
[58] Field of Search .......... 435/240.2, 240.23, 240.24, 435/240.241, 240.243, 284–287, 310; 210/500.25

[56] References Cited

U.S. PATENT DOCUMENTS

| | | | |
|---|---|---|---|
| 4,043,869 | 8/1977 | Barker et al. | 435/183 X |
| 4,446,234 | 5/1984 | Russo et al. | 435/240.241 X |
| 4,514,499 | 4/1985 | Noll | 435/240.23 |
| 4,608,342 | 8/1986 | Nees | 435/284 X |
| 4,757,017 | 7/1988 | Cheung | 435/240.23 |
| 4,762,619 | 8/1988 | Gaddis | 210/500.25 X |

OTHER PUBLICATIONS

Van Nostrand Reinhold, *The Condensed Dictionary*, 1981, p. 74.

*Primary Examiner*—Robert J. Warden
*Assistant Examiner*—Rebekah A. Griffith
*Attorney, Agent, or Firm*—Cooper & Dunham

[57] ABSTRACT

A method of growing or maintaining mammalian cells comprises applying a culture of the cells to a surface of a porous inorganic membrane support. The support is preferably a transparent anodic aluminium oxide membrane. The support carrying cells (44) growing or being maintained thereon may comprise a short tube (30) and a disc (32) of the porous inorganic membrane, the disc being sealed round its periphery to the tube adjacent one end thereof.

10 Claims, 2 Drawing Sheets

POROUS INORGANIC MEMBRANE SUPPORT AND METHOD

This invention concerns the us inorganic membrane supports for the growth of animal and plant cells. Some cells, such as fibroblast and transformed cells are relatively easy to culture. They attach and proliferate on various solid surfaces (e.g. plastics or glass) and can even grow in suspension. However, other mammalian cells such as differentiated cells derived from epithelial tissues are anchorage dependent and difficult to grow. (Differentiated cells are those which have specific functional characteristics. Most cells in multicellular organisms are differentiated, e.g. blood cells, nerve cells and muscle cells of mammals). Furthermore, epithelial cells, when grown on impermeable surfaces may not develop differentiated characteristics.

However it has been observed that when epithelial cells are grown on permeable supports they may develop differentiation. This may be attributable to the fact that permeable supports allow the cell to receive nutrients through both upper and lower surfaces.

The use of membranes in tissue culture for support of keratinocytes has been described by F.L.Vaughan, R.H.Gray and I.A.Bernstein (In Vitro Cellular and Developmental Biology, 22, pages 141 to 149, 1986). The authors monitored the attachment, proliferation and differentiation of primary cultures of keratinocytes after seeding and incubation on various synthetic organic membranes. Attempts to obtain satisfactory attachment to two membranes were unsuccessful. Membranes specifically prepared for tissue culture procedures supported attachment and proliferation equal to, or better than, the plastic culture vessels used as controls. None of the three transparent membranes tried, supported attachment and proliferation as well as the plastic culture vessels used as controls. Somewhat improved results were obtained by pre-coating the membranes with fibronectin.

In one aspect this invention provides a porous inorganic membrane support carrying cells growing or being maintained thereon. In another aspect, the invention provides a method of growing or maintaining cells by applying a culture of the cells to a porous inorganic membrane support and maintaining the cells under conditions to cause them to grow on the support.

Advantages of using inorganic membrane supports are that they are generally inert and non-toxic to the cells and can generally be heated or otherwise sterilized without damage. The membrane supports may be formed of various materials, including metal oxides such as zirconium oxide and, more particularly, aluminium oxide. Porous inorganic membranes of this kind are described in the literature For example, alumina and other metal oxide membranes can be made by a sol-gel technique as described by A.F.M.Leenaars et al. in the Journal of Material Science, 19 (1984) 1077 to 1088; or by a tape-casting technique as described by R.E.Mistler et al. at pages 411 to 448 of the book "Ceramics Processing Before Firing", edited by G.Y.Onoda et al. Wiley, N.Y., 1978. Porous membranes may be made by the methods described in EPA 224443 and 224444. Preferably, an anodic aluminium oxide membrane is used.

When an aluminium substrate is anodized in certain electrolytes, e.g. dilute sulphuric acid, a porous anodic oxide film is formed on its surface, consisting largely of amorphous alumina. The pores extend from the outer surface of the film to near the metal/oxide interface. Adjacent the metal/oxide interface is a thin coherent layer of anodic oxide (the barrier oxide layer). The anodic oxide membrane can be separated from the metal substrate on which it was formed by several techniques, all of which give rise to symmetric membranes having generally cylindrical pores extending from one surface to the other and of generally uniform diameter throughout their length.

EPA 178831 describes how porous membranes can be formed by separating conventional anodic aluminium oxide membranes from their metal substrate by a slow voltage reduction technique designed to thin the barrier layer and eventually to dissolve any of the remaining barrier layer at the metal/oxide interface. The resulting asymmetric anodic aluminium oxide membranes have pores extending from one face of the membrane to the other, including a system of larger pores extending in from one face and interconnecting with a system of smaller pores extending in from the other face.

Stripped porous anodic aluminium oxide films, either of the symmetric or the asymmetric sort, are particularly suitable as tissue culture supports by virtue of the following properties:
  they are highly porous;
  they are generally transparent, which permits microscopic observation of cells in situ;
  they are smooth;
  they are rigid, therefore allowing physical transfer of complete cell monolayers;
  they are non-toxic;
  they are not readily attacked by organic chemicals, which may be important for processing of the cells for observation;
  they are sterilizable e.g. by autoclaving or by U.V. or gamma radiation.

The low porosity of some organic membranes commercially available for tissue culture purposes can under some circumstances restrict cell growth. This problem does not arise with anodic aluminium oxide membranes which can be arranged to be highly porous. Pore size in such membranes can be readily controlled by control of the anodizing conditions. In general, pores should be small enough to support growing cells, so that the cells sit on the surface of the membrane. In some circumstances, the pores may need to be large enough to permit the passage of cell nutrients including proteins up to 150 kDa. In general, anodizing conditions and electrolytes do not appear critical. We have grown cells with equal success on membranes with pores 0.2 microns and 0.02 microns diameter, formed by anodizing in phosphoric acid and mixed electrolytes. Membrane thickness is also not critical, though thicker membranes have the advantage of improved rigidity, while thinner membranes may have better light-transmitting properties. Membranes may be flat, or may be profiled, for example as described in European Patent 87303336.

Although the nature of the cells grown on the support membranes is not critical, the invention is particularly concerned with growth of mammalian cells. The invention is likely to be particularly useful for growing anchorage dependent cells, i.e. cells which will not grow, or will lose their differentiated characteristics, in suspension. The invention is applicable to transformed, and more particularly to differentiated, cells. Examples of cell lines are given in the experimental section below. The invention is of particular value for growing or maintaining fastidious cell types such as rat hepatocytes. Human pancreas islets have been maintained on a porous anodic aluminium oxide membrane support.

Conditions for cell growth are not critical, and can be those conventionally used. In Example 2 below is reported the observation that a particular cell line was found to grow on an anodic aluminium oxide membrane in a medium containing only 2.5% foetal calf serum, where these cells would not grow on a conventional plastic support at this serum concentration. This isolated observation may be an indication that the use of porous inorganic membrane supports according to this invention may enable cell growth to take place in the presence of lower serum concentrations.

It is found that mammalian cells adhere readily to the porous inorganic membrane supports used in this invention. This was not predictable. For example, it is known that mammalian cells will only adhere to glass supports if they have been very thoroughly cleaned beforehand. It is conventional practice to pre-coat porous supports in order to improve cell adhesion, for example using collagen, laminin or fibronectin. However, pre-coating in this way is not only tiresome, but also creates problems when cells are subsequently stained for microscopic observation. For example collagen coatings interfere with collagen staining procedures. Indeed, some organic tissue culture supports give rise to staining problems even when uncoated.

It has been found that the porous inorganic membrane supports used in this invention in general give good adhesion properties for cells without the need for pre-coating. However, if desired, the supports may be pre-coated, for example with the materials noted above. Or the support may carry an adherent monolayer of cells, which itself acts as a support for further cells of different origin. Alternatively, the monolayer of cells may be removed to leave just a baso-lateral membrane on the inorganic support, to which the cells of different origin may be applied.

A great advantage of using a transparent membrane support is that the growing cells can be observed in situ by phase contrast or normal transmission light microscopy. To maintain sterility while the cells are immersed in liquid culture medium the cells are viewed from underneath through the membrane support, with illumination being provided from above. Cells can be prepared for light microscopy, or for scanning electron microscopy (SEM) by standard techniques. Exceptionally good images can be obtained by SEM using these supports. A protocol for fixing and staining cells for light microscopy is given below.

In order to perform the invention, a piece of the membrane support may be placed in a standard tissue culture vessel and a suspension of cells in growth medium applied to the upper surface. The culture vessel is closed and incubated under suitable conditions. If this arrangement does not provide sufficient access for culture medium through the porous membrane supports to the growing cells, the problem can be remedied by supporting the membrane slightly above the floor of the tissue culture vessel. This is best achieved by attaching the membrane disc to one end of a short length of plastic tube to form an open-top cylinder whose diameter is considerably greater than its length. This cylinder is provided with feet surrounding the disc of support membrane, and is hereinafter called a culture insert. This comprises a short tube whose diameter is typically greater than its length and a disc of a porous inorganic membrane such as a porous anodic aluminium oxide membrane, the disc being sealed round its periphery to the tube adjacent one end thereof, and living cells maintained on (e.g. adhered to) the membrane within the tube.

It may be advantageous to provide different media adjacent the lower and upper surfaces of the porous membrane support. For example, the culture medium adjacent the lower surface may contain the nutrients necessary for cell growth, which can reach the growing cells by passing through the pores of the membrane support. The cells may produce metabolites of large molecular weight, perhaps too large to diffuse readily through the narrow pores of the support membrane. The liquid medium adjacent the upper surface of the support membrane may contain these metabolites and thus be of different composition from that adjacent the lower surface. This feature may be useful to determine the viability or properties of the growing cells.

BRIEF DESCRIPTION OF THE DRAWINGS

Reference is directed to the accompanying drawings in which:

FIG. 1 is a set of diagrams to show proposed use of porous inorganic membranes as supports for anchorage dependent cells.

Referring to FIG. 2, a culture insert comprises a length of generally cylindrical plastic tubing 30 whose diameter is greater than its length; a porous inorganic membrane disc 32 sealed, round the periphery, inside the plastic tube adjacent its lower end, the tube being recessed to receive the membrane; and feet 33 to raise the membrane off the floor. A culture plate comprises a floor 34, walls 36 defining individual wells of which one is shown, and a plate lid 38. The well has been partly filled with culture medium 40. The culture insert has been placed in the well such that the medium 40 contacts the lower surface only of the membrane. Another medium 42, of the same or different composition has been placed in the culture insert. A monolayer of cells 44 is adhered to the upper surface of the membrane and is in contact, through the pores of the membrane, with the culture medium 40.

Figure 1A:
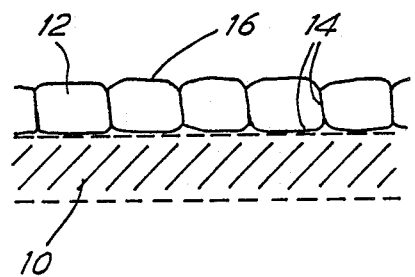
FIG. 1a shows a membrane support 10 carrying a monolayer 12 of epithelial cells, including a baso lateral membrane 14 and a luminal membrane 16.
Figure 1B:
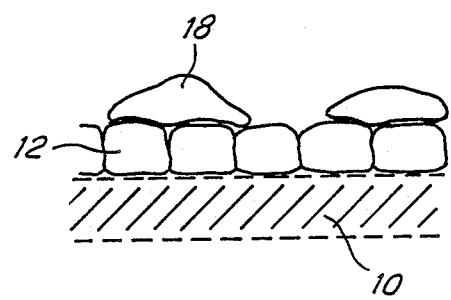
FIG. 1b shows this complete set-up acting as support for a further layer 18 of cells of different origin, e.g. sebacytes.
Figure 1C:
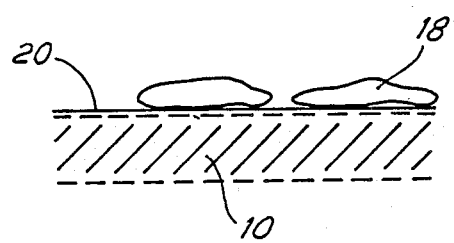
FIG. 1c shows an arrangement in which the epithelial cells have been killed to leave a basement membrane 20 to which the sebacyte cells 18 have adhered.
Figure 2:
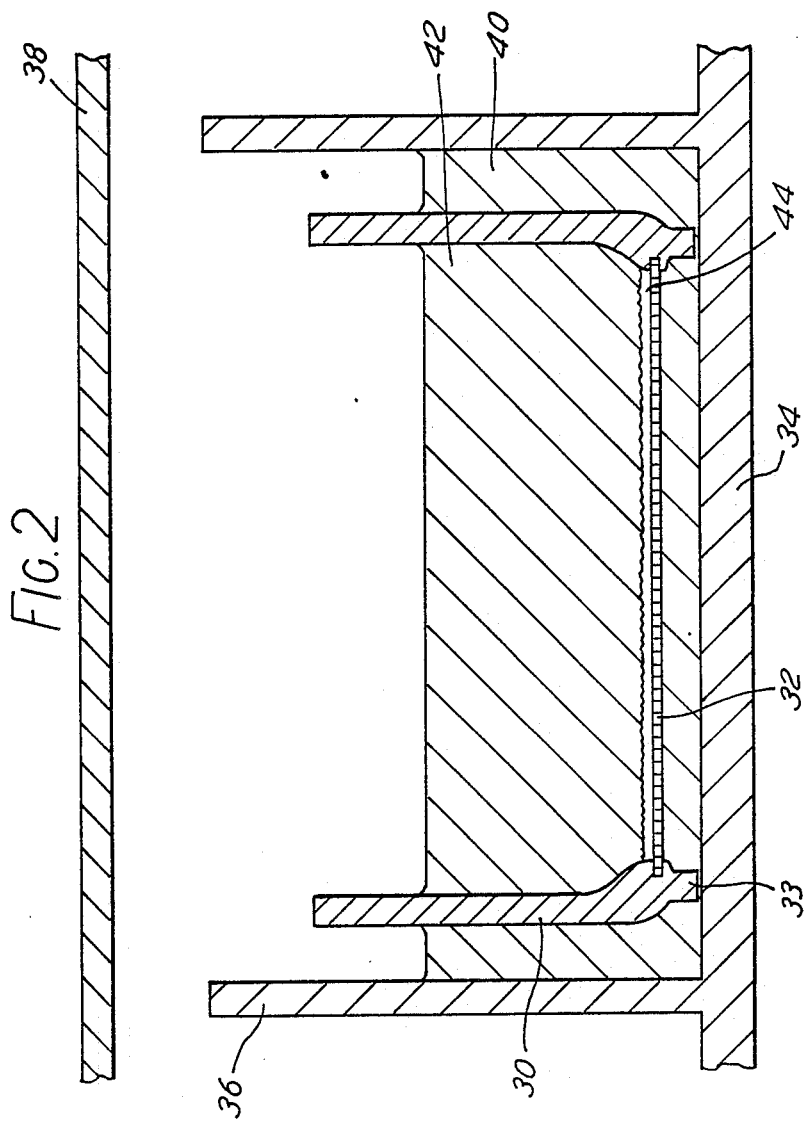
FIG. 2 is a sectional side elevation of a culture insert in one well of a tissue culture plate.

The following examples illustrate the invention.

EXAMPLE 1

Three cell types were used.
Madin Darby Canine Kidney—(MDCK)
Mouse Embryo Fibroblast—(3T3)
Bovine Corneal Endothelial—(BCE) Primary
The medium formulation for BCE cells was:
William E basal medium (without glutamine) 100ml
Insulin 10 µg/ml
Transferrin 10 µg/ml
Penicillin/Streptomycin
Fungizone
Hydrocortisone (10ng/100ml)

Glutamine
Epithelial growth factor (10ng/ml)
Trace elements
Foetal calf serum 10%.

For MDCK and 3T3 cells the medium formulation was the same with the omission of transferrin, hydrocortisone and epithelial growth factor.

The anodic oxide membrane used was a mixed phosphoric and oxalic acid type, both 0.2 µm and 0.02 µm pore size (designated 0.2 ME and 0.02 ME respectively in the Tables below).

Cells were routinely seeded onto 11 mm discs in 24 well tissue-culture trays at a density of $10^4$ cells/ml (1ml per well). As controls, cells were seeded at the same density into wells without membrane.

The viability of cells which had been grown on plastic or membrane was determined by trypsinization, trypan blue staining and counting of stained and unstained cells. Results are shown in Table 1.

This shows that there is no significant difference in viability of all three cell types following the enzymological release from sustrates studied. This indicates that the membrane may be treated as a plastic substrate when subculturing.

TABLE 1

| | % Viability ± s.e.m (n = 3) of Three Cell Types on Different Substrates | | |
|---|---|---|---|
| Cell Type | Plastic | 0.2ME | 0.02ME |
| MDCK | 83% ± 11.9 | 72% ± 14.9 | 70% ± 6.7 |
| 3T3 | 70% ± 3.8 | 66% ± 4.8 | 81% ± 15.4 |
| BCE | 95% ± 5.2 | 81% ± 7.6 | 76% ± 2.3 |

The rate and efficiency of cell attachment onto Anopore or plastic was determined after seeding at $10^4$ cells/well.

Table 2 shows that all three cell types seed equally well on both plastic and 0.02 µm membrane. However cells grown on the 0.2 µm membrane show a significantly reduced seeding efficiency by both MDCK and BCE. This shows, therefore, that the 0.02 µm ME membrane has a greater capacity for cell attachment than plastic. However the 0.2 µm ME membrane has less.

TABLE 2

| | % Seeding Efficieny Standard Error of the Mean (s.e.m) n = 3 | | |
|---|---|---|---|
| Cell Type | Plastic | 0.2ME | 0.02ME |
| | 4 Hours | | |
| MDCK | 33% ± 12.1 | 21% ± 10.4 | 26% ± 6.6 |
| 3T3 | 14% ± 4.8 | 11% ± 5.4 | 19% ± 3.9 |
| BCE | 29% ± 5.5 | 16% ± 7.1 | 31% ± 8.6 |
| | 8 Hours | | |
| MDCK | 39% ± 3.6 | 21% ± 11.1 | 26% ± 6.4 |
| 3T3 | 24% ± 6.9 | 19% ± 2.3 | 25% ± 1.8 |
| BCE | 41% ± 7.8 | 27% ± 3.6 | 35% ± 5 |

Cells were grown on plastic and both 0.2 µm and 0.02 µm ME membranes for 7-10 days, then subcultured onto their respective substrates at a high inoculum. The cells recovered in the supernatant after 4 and 8 hours, were then counted, and the seeding efficiency calculated as 100× (total cells seeded minus cells in supernatant)/Total Cells Seeded.

Plating efficiency was also determined. 1ml of cell suspension (2-50 cells/ml) was placed in empty wells of a 24 well tray and wells containing membrane discs. The plating efficiency is calculated from the number of colonies of 16 cells or more that grow after 5 days.

$$\frac{\text{No. of colonies formed}}{\text{No. of cells seeded}} \times 100 = \text{plating efficiency.}$$

Table 3 shows that the plating efficiency of cells grown on plastic and both 0.2 µm and 0.02 µm membranes compare favourably. Indeed cells grown on 0.02 µm membrane plate at a significantly higher rate than on plastic. This shows, therefore, that anodic oxide membranes promote the growth of cells as efficiently as does plastic.

Observations showed that confluence on anodic oxide membrane is generally attained by 10-14 days, and this also compared very well with plastic.

TABLE 3

| | % Plating Efficiency ± s.e.m (n = 3), of Three Cell Types on Different Substrates | | |
|---|---|---|---|
| Cell Type | Plastic | 0.2ME | 0.02ME |
| MDCK | 23% ± 4.3 | 19% ± 6.2 | 27% ± 7.83 |
| 3T3 | 11% ± 2.1 | 9% ± 1.9 | 19% ± 5 |
| BCE | 17% ± 2.2 | 17% ± 3.7 | 28% ± 1.5 |

TEM examinations of BCE cells demonstrated that they were clearly polarized and possess tight junctions.

EXAMPLE 2

The following cells lines were grown:
Madin Darby Canine Kidney (MDCK) - anchorage dependent.
Bovine Corneal Endothelial (BCE) - anchorage dependent.
Mouse plasmacytoma (X63-AG8-6SS) - non-anchorage dependent.
Mouse hybridoma PF - non-anchorage dependent.
Mouse hybridoma 3C3 - non-anchorage dependent.

Porous anodic aluminium oxide membranes were sterilized by autoclaving, immersion in absolute ethanol or by U.V. radiation. Alternatively, culture inserts (open-top vessels comprising a short length of plastic tube closed at the bottom by a disc of the membrane) were supplied pre-sterilized by gammaradiation.

Sterile flat sheet membranes or culture inserts were placed in 24-well or 6-well tissue culture plates before seeding with a cell suspension.

In order to sub-culture cells, monolayers of MDCK or BCE cells were stripped in sterile buffered EDTA containing trypsin (52 µg/ml). Mouse plasmacytoma and hybridoma cell lines could be removed simply by gentle shaking of the culture vessel or by pipetting. Cells were incubated at 37° C. and 5% $CO_2$/95% air. Medium used for all cell lines contained:
Dulbecco's minimal essential medium (DMEM)
10% Foetal calf serum (FCS)
4mg/1 gentamycin sulphate.

All cell types were found to grow well both on flat sheet membrane and culture inserts. Cell monolayers were visualized by normal light microscopy (both unstained and after staining) and by SEM. Protocols were developed for staining cells for light microscopy (see below) and for preparation for SEM.

BCE cells were found to grow on the insert devices with 2.5% foetal calf serum. These wells will not grow on plastic supports at this serum concentration.

EXAMPLE 3

The following cell lines were grown:
Bovine corneal endothelial cells (BCE)

Baby hamster kidney (BHK)
Primary rat brain cells.

Growth media used for BCE and BHK was Glasgow modification of Eagles medium. For rat brain cells the growth medium was DMEM. 10% foetal calf serum was used in all cases. Cells were supported on culture inserts and cultures incubated at 37° C. and 5% $CO_2$/95% air.

All cells grew well on the insert devices. Immunofluorescent staining protocols have been developed for both BHK and rat primary brain cells grown in this way.

There follow notes on protocols for fixing and staining cells on porous transparent inorganic support media for light microscopy.

Fixatives which may be used include para-formaldehyde, formaldehyde, methanol and glutaraldehyde, with 2% para-formaldehyde in PBSA being preferred. Stains which may be used include Weigart's/Van Geeson; Giemsa; Giemsa/light green; Leishmans; hematoxylin/eosin; preferred being Weigert's/Van Geeson (stains nuclei purple and collagen pink). There follows a protocol for permanent staining of cell cultures for light microscopy.

Materials
1. 2% paraformaldehyde in PBS, pH7.3
2. Weigert's iron hematoxylin prepared as follows:

Solution A: 1 gram hematoxylin, 100 ml absolute alcohol,

Solution B. 4ml aqueous ferric chloride (30%), 1ml concentrated HCl, 95ml distilled water, Filter solutions through glass fibre paper (2X). Mix equal volumes of solutions A and B. Use immediately.

3. Van Geeson's stain prepared as follows: 100ml saturated picric acid 5 to 10ml acid fuchsin (1%)

Filter as above.

4. Ethanol (30, 50, 70, 90 and 100%)
5. "Histo-clear" (from National Diagnostics, New Jersey USA.)
6. DePeX mountant (BDH Chemicals Ltd.)

Method (Perform complete staining protocol on intact tissue-culture inserts).

1. Fix wet membrane in 2% paraformaldehyde in PBS (pH7.3). 1 hour to 24 hours at 37° C.
2. Wash thoroughly in distilled water.
3. Stain in freshly mixed Weigert's iron haematoxylin for 5 to 10 minutes.
4. Wash thoroughly in distilled water.
5. Stain in Van Geeson's stain for up to 10 minutes.
6. Wash thoroughly in distilled water.
7. Dry in graded ethanol (30, 50, 70, 90 and 100%) for 2 minutes each.
8. Air dry.
9. Dip in "Histo-Clear"
10. Mount membrane between slide and coverslip in DePeX mountant.

EXAMPLE 4

MDCK cells were grown on Dulbecco's minimal essential medium (DMEM), 10% foetal calf serum, and 4 mg/l gentamycin sulphate.

The anodic oxide membranes used (0.2$\mu$m and 0.02$\mu$m pore size and 25 mm diameter) were supported in devices (inserts) as described above.

MDCK cells were seeded at $2 \times 10^{44}$ cells/cm$^3$ into 25mm inserts in wells of 6 well tissue culture trays or directly into wells. Total seeding into the wells was approximately twice that required for the insert. The total volume of medium used in both cases was 3 ml/well (when using inserts the levels equilibriate between the inner and outer chambers).

Growth curves were constructed for cells on plastic and on oxide membranes. Cell numbers were estimated using a spectrophotometric method described below. Medium was aspirated from the wells or inserts and retained (to count any loose cells in suspension). 5 ml 0.05% w/v trypsin in 0.04% EDTA solution was added to the monolayers, left for 30 seconds and decanted off. The monolayers were then left for 5-7 minutes at 37° C. and 10 ml solution A+10% foetal calf serum added. Cells were resuspended by gentle pipetting using an Ependorf pipettor. Cell concentration and viability were determined using Erythrocin B dye exclusion and an improved Neubauer chamber.

A standard curve for conversion of optical density (OD) to cell number is produced by adjusting the concentration of the cell suspension to the desired top standard ($5 \times 10^5$ cells/ml) with solution A+10% FCS, and preparing a series of doubling dilutions down to $10^4$ cells/ml. The optical density of cell suspensions is then read at 780 nm against a blank of solution A+10% FCS.

5 replicate cultures on the three surfaces (0.2 and 0.02 $\mu$m membranes and plastic) were assayed by OD and this measurement converted to cell number. Results are set out in Table 4.

Results indicate that growth on the anodic oxide membranes is faster than on plastic and that a higher cell yield is attained. 0.02 $\mu$m membranes appear to be better than 0.2 $\mu$m membranes.

TABLE 4

| | Viable Cells/cm$^2$ ($\times 10^4$) | | |
|---|---|---|---|
| Days | Plastic | 0.2 microns | 0.02 microns |
| 1 | 2 | 2 | 2 |
| 4 | 8.5 | 6.5 | 9.5 |
| 7 | 17.5 | 12 | 15 |
| 11 | 16 | 19 | 26.5 |

EXAMPLE 5

Rat parenchymal hepatocytes were isolated either by conventional collagenase perfusion technique or by digitonin/collagenase perfusion.

The hepatocytes were cultured in monolayer on anodic oxide membranes (25 mm inserts containing 0.2 $\mu$m membranes) and compared TM with monolayers on conventional tissue culture dishes (Lux).

Two hours after seeding the plating efficiency was determined enzymatically. The medium was aspirated from the plates or inserts and an aliquot sedimented (100g/2m). A further aliquot was sonicated. Lactate dehydrogenase activity was determined and the difference in activity (total suspension—supernatant) used as an index of unattached cells.

The percentage of unattached cells after 2 hours was similar for the membrane and dish culture, suggesting a similar plating efficiency.

After hepatocyte attachment (4 hours) the monolayers were cultured for 20-48 hours and the metabolic performance of the hepatocytes was assessed by monitoring the metabolism of specific substrates. The rates of substrate metabolism and product formation were determined. The rates of fatty acid metabolism to ketone bodies were similar in monolayers on anodic oxide membranes and on culture dishes (Table 5). Rates of mitochondrial pyruvate metabolism and conversion to lactate were, however, higher in the monolayers on Anopore membranes (Table 6).

Results therfore indicate that the anodic oxide membrane will act as a good support for hepatocyte culture and that certain metabolic activities are increased on this support, compared with conventional plastic.

TABLE 5

Formation of ketone bodies from palmitate or octanoate in hepatocyte monolayers on culture dishes and anodic oxide membranes.

| Substrate: | Culture dishes | Membranes |
|---|---|---|
|  | (nmol/culture/h) | |
| (1) 0.75 mM-Palmitate + 1 mM-pyruvate | | |
| Expt. 1 (Total cells) | (3) 141 ± 3 | (3) 167 ± 24 |
| Expt. 2 (Periportal) | (4) 158 ± 10 | (4) 158 ± 13 |
| Expt. 3 (Perivenous) | (4) 129 ± 5 | (4) 115 ± 10 |
| (2) 1 mM-Octanoate | | |
| Expt. 1 (Total cells) | (3) 108 ± 4 | (3) 109 ± 15 |
| Expt. 2 (Total cells) | (5) 174 ± 12 | (5) 192 ± 21 |

Hepatocyte monolayers isolated from whole liver or from the periportal or perivenous zone were cultured for 20h with dexamethasone and insulin. The rate of formation of detone bodies (acetoacetate + 3-hydroxybutyrate) was determined during a 2h incubation with either 0.75mM-palmitate, 1mM-pyruvate and 0.5mM-L-carnitine or with 1mM-octanoate. Values are means ±S.D. for the number of culture dishes or membranes shown in parenthesis.

TABLE 6

Mitochondrial pyruvate metabolism and conversion to lactate in hepatocyte monolayers on culture dishes and anodic oxide membranes.

| | Culture dishes | Membranes |
|---|---|---|
|  | (nmol of pyruvate/culture/h) | |
| Expt. 1 (Perivenous) | | |
| Mitochondrial pyruvate metabolism | (4) 106 ± 8 | (4) 232 ± 36 |
| Lactate formation | 250 ± 8 | 306 ± 18 |
| Expt. 2 (Periportal) | | |
| Mitochondrial pyruvate metabolism | (4) 230 ± 32 | (4) 386 ± 12 |
| Lactate formation | 144 ± 30 | 150 ± 10 |
| Expt. 3 (Total) | | |
| Mitochondrial pyruvate metabolism | (3) 154 ± 8 | (3) 194 ± 15 |
| Lactate formation | 152 ± 23 | 250 ± 17 |
| Expt. 3 + Glucagon | | |
| Mitochondrial pyruvate metabolism | (3) 178 ± 6 | (3) 234 ± 10 |
| Lactate formation | 193 ± 7 | 302 ± 8 |

Hepatocyte monolayers were cultured for either 20h (Expts 1 & 2) or 48h (Expt 3) in serum-free medium with 10nM-dexamethasone + 10nM-insulin or with the additional presence of glucagon (100nM). Pyruvate metabolism was determined during a 2h incubation with 1mM-Pyruvate and 0.75mM-palmitate. The rate of mitochondrial pyruvate metabolism was determined from the decrease in the concentration of pyruvate that could not be accounted for as either lactate or alanine. Rates are expressed as nmol of pyruvate metabolised per h per culture. Values are means ± S.D. for the number of culture dishes or membranes shown in parenthesis.

EXAMPLE 6

Assessment of the growth of Chinese hamster ovary (CHO) cells on anodic oxide membranes compared with plastic.

Protocol:

100 CHO cells (as assessed by counting with haemocytometer) from a routinely grown culture were used to inoculate each membrane immersed in the laboratory standard MEM medium supplemented with foetal calf serum.

Cells were incubated for four days with daily monitoring of the growth. At 24 hour intervals sample membranes and control wells were trypsinized to detach the cells and the cell numbers per membrane (or per well) estimated by haemocytometer counting in order to obtain an estimation of the relative doubling times of the cells. All cultures were examined by light microscopy daily, and at the end of the growth period representative samples were harvested and used to inoculate a further set of membranes in order to establish that the cells remained healthy and capable of re-establishing after growth under the test conditions.

For each observation 5 samples were taken from a stock of parallel cultures inoculated at a single timepoint.

Membranes used in the test:
(a) Anodic oxide 0.02 μm pore size
(b) Anodic oxide 0.2 μm pore size
(c) Control culture grown on routine laboratory plastic surface.

Observations.

The CHO appeared to adhere and grow well on the anodic oxide membranes and detaching at subculturing with trypsin in a routine manner worked as well as when cells were taken from conventional tissue membranes with no abnormal cells detected; colony formation also appeared to be unaltered. The mean and standard deviations of all the cell counts were obtained. Statistical analysis failed to reveal any significant differences in the growth-rates of the cultures of CHO cells on the different surfaces.

EXAMPLE 7

Growth of MDCK and BCE cells on anodic oxide membranes and preparation for light and electron microscopy.

MDCK and BCE cells were grown on 25mm diameter membranes as described previously (Example 1).

It is possible to observe cells simply using phase contrast microscopy. There is little, if any, loss of definition of image compared with that on plastic. In addition to those stains listed in Example 3, the following stains have also been used successfully with cells on the anodic oxide membrane:

Wiegerts / Van Gieson + light green
Wiegerts / Van Gieson + neutral red
Celestine blue + Mayers haematoxylin
Heidenhains haemotoxylin + iron alum.

Using the above stains, background staining of the membrane itself is minimal and visualization of cellular components is as good as that on plastic or glass. The transparency of the membrane is an extremely important advantage. Further immuno-fluorescent staining of BHK and CHO cells on the membranes has been carried out. An image of high contrast with minimal background fluorescence has been obtained.

A suitably stained membrane may be mounted on a microscope slide beneath a coverslip using standard procedures. No deterioration of preparation occurs other than fading of the stain as is normal with such preparations after a period of time.

Basic SEM preparation procedures have been established for cells grown on anodic oxide membranes.

The inorganic membrane is resistant to organic chemicals used in SEM preparation procedures, therefore making it extremely versatile in use. The rigidity of the membrane also makes handling easier than with organic polymer membranes used for cell culture. A tool has been specially manufactured to break-out the membrane from the insert device as an intact circular disc. This disc is approximately 22 mm in diameter and will fit into standard stainless steel sample holders used for preparation of multiple samples (membranes) for electron microscopy.

We claim:

1. A method of growing or maintaining cells by means of a porous inorganic support, which comprises applying a culture of the cells to a surface of a porous inorganic membrane support and maintaining the cells under conditions to cause them to grow or be maintained on the support.

2. A method as claimed in claim 1, wherein the membrane support is transparent.

3. A method as claimed in claim 1, wherein the cells are mammalian cells.

4. A method as claimed in claim 1, wherein the membrane support is of alumina.

5. A method as claimed in claim 4, wherein the alumina membrane is an anodic aluminium oxide membrane.

6. A porous inorganic membrane support carrying cells growing or being maintained on the surface thereof.

7. A support as claimed in claim 6, formed by applying a culture of cells to a surface of a porous inorganic membrane support and maintaining the cells under conditions to cause them to grow or be maintained on the support.

8. A support as claimed in claim 6 comprising a short tube (30) and a disc (32) of the porous membrane, the disc being sealed round its periphery to the tube adjacent one end thereof, the living cells being maintained on the membrane within the tube.

9. Apparatus for growing cells comprising a porous inorganic membrane support (32) having a first face in contact with a first liquid medium (40) and a second face to which the growing cells (44) adhere in contact with a second liquid medium (42), wherein the first liquid medium is not in communication with the second liquid medium except through the porous support.

10. Apparatus as claimed in claim 9, wherein the second liquid medium is of different composition from the first liquid medium.

* * * * *